United States Patent [19]

Jones

[11] Patent Number: 4,892,766
[45] Date of Patent: Jan. 9, 1990

[54] CAPSULES

[75] Inventor: Brian E. Jones, Basingstoke, England

[73] Assignee: Lilly Industries Limited, Basingstoke, England

[21] Appl. No.: 241,647

[22] Filed: Sep. 8, 1988

[30] Foreign Application Priority Data

Sep. 11, 1987 [GB] United Kingdom ................. 8721455

[51] Int. Cl.⁴ ................................................ A61K 9/48
[52] U.S. Cl. .................................. 428/36.4; 106/125; 106/128; 106/136; 206/528; 220/8; 424/453; 424/456; 428/321.5; 428/478.2; 428/478.4
[58] Field of Search ................. 428/36.4, 321.5, 478.2, 428/478.4; 424/453, 456; 264/4; 206/528; 220/8; 106/125, 136, 128

[56] References Cited

U.S. PATENT DOCUMENTS

| | | | |
|---|---|---|---|
| 2,441,927 | 10/1942 | Adams | 106/128 |
| 2,491,475 | 3/1946 | Bogin | 424/453 |
| 2,575,789 | 11/1948 | Bogin | 106/128 |
| 2,580,683 | 1/1952 | Krueger | 99/165 |
| 2,667,268 | 1/1954 | Griffin | 206/84 |
| 2,990,334 | 6/1961 | Graham | 167/83 |
| 3,444,290 | 2/1966 | Wai | 206/528 |
| 3,539,361 | 11/1970 | Coleman | 428/478.4 |
| 3,927,195 | 12/1975 | Messora | 220/8 |
| 4,500,358 | 2/1985 | Mayer et al. | 424/453 |
| 4,591,475 | 5/1986 | Tomka et al. | 424/456 |
| 4,744,988 | 5/1988 | Brox | 424/456 |
| 4,755,389 | 5/1988 | Jones et al. | 424/456 |

FOREIGN PATENT DOCUMENTS

| | | | |
|---|---|---|---|
| 752362 | 7/1956 | United Kingdom | 81/1 |
| 1341121 | 12/1973 | United Kingdom | |

OTHER PUBLICATIONS

Martindale, The Extra Pharmacopoeia, 28th ed., edit. by James E. F. Reynolds, pp. 950-951.
Chemical Abstracts, vol. 107, No. 19, Nov. 9, 1987, p. 133, 107:178356m & 107:178357n.

Primary Examiner—Ellis P. Robinson
Assistant Examiner—Archene A. Turner
Attorney, Agent, or Firm—Douglas J. Taylor; Leroy Whitaker

[57] ABSTRACT

Hard gelatin capsules are made from gelatin containing up to 10% of a preferably hydrophilic fibrous material. They do not split after storage when filled with hygroscopic or deliquescent materials.

12 Claims, No Drawings

CAPSULES

This invention relates to capsules of the sort used to contain measured doses of pharmaceutical or veterinary compositions, and in particular to two-piece hard gelatin capsules.

Such capsules are manufactured, for example, by dipping mould pins into a hot solution of gelatin, removing the pins from the gelatin solution, allowing the gelatin on the pins to set by drying, and stripping the so-formed shells from the pins. Water is lost in the drying process, resulting in a hard gelatin shell with an equilibrium water content of about 13-16%.

Removal of further amounts of water from the capsule shells results in the gelatin walls becoming brittle. If this occurs after filling and assembly of the capsules it an lead to loss of the contents of the capsule because of damage due to mechanical handling during packing or to undue pressure on the capsule wall during removal from the packaging.

Loss of water, and consequent embrittlement, can be caused by a number of factors. Thus the capsules may be stored or transported before or after filling and assembly in unsuitable ambient conditions leading to loss of water to the atmosphere. Equally, it may be desired to encapsulate hygroscopic or deliquescent materials to prevent them absorbing moisture from the atmosphere with possible degradation. However, if hard gelatin capsules are used for this purpose, there is a tendency for the hygroscopic or deliquescent contents to draw water out of the gelatin of the capsule. This may then cause embrittlement and possibly lead to the capsules being damaged and the contents lost or spoiled. The risk of damage to capsules is particularly high during removal from blister packages, when unusual stresses are applied to the capsule shells. Thus two-piece gelatin capsules which contain a hygroscopic or deliquescent material and have been supplied in blister packs may become brittle during the period between manufacture and use, with the result that when the user attempts to remove the capsule from the blister pack, the stresses applied to the capsule may cause it to crack and rupture, with loss of the contents.

Attempts have been made to overcome the problem of embrittlement of hard gelatin capsules. For example, one approach has been to add plasticisers such as glycerin, sorbitol or other polyols to the gelatin solution from which the capsules are formed. Such plasticisers are commonly used in the manufacture of one-piece, soft gelatin capsules. Another approach has been to incorporate material such as diethyl phthalate or triacetin, which are used as plasticisers in the film-coating of tablets.

None of the attempts made have so far produced satisfactory hard gelatin capsules which can be stored with hygroscopic or deliquescent contents without becoming brittle. The above-proposed solutions either lead to weakened capsules or prove impossible to carry out because of problems of polymer incompatibility.

We have now discovered a method of providing two-piece hard gelatin capsules which overcomes the problem of embrittlement and splitting of the capsule walls after storage when used to contain hydroscopic or deliquescent materials.

This invention therefore provides a two-piece hard capsule shell comprising an admixture of gelatin and a fibrous material. As used in the present invention, the term "two piece capsule shell" means a capsule comprised of a cylindrically shaped body and cap both of which have an open end and a closed end, the body of smaller diameter than the cap so that the cap may enclose the open end of the body by sliding the cap onto the body. The fibrous material is preferably hydrophilic and one which sells when it absorbs water. The fibrous material is present in the gelatin in addition to the normal excipients and additives such as, for example, colouring agents, wetting agents, preservatives, and the like.

The amount of the fibrous material which is added to the gelatin is not critical. Thus it may, for example, be present in an amount up to about 10%. It is preferably present in an amount up to about 5% by weight, and more preferably from about 0.5% to about 2.0%. The optimum amount will depend to some extent on the properties of the selected fibrous material, and can readily be determined by the skilled man.

The fibrous material is used as a powder, the lengths of the fibres being below about 1000 microns, the preferably up to about 300 microns, for example, from about 50 microns to about 300 microns.

As an example of such a material may mentioned Croscarmellose (USNF), a cross-liked form of carboxymethylcellulose sodium as supplied, for example, by FMC as "AcDiSol" for use as a table disintegrant and dissolution enhancer. This is a fibrous material, consisting of fibres of 50-300 microns in length, and has the properties of a) swelling when brought into contact with water and b) retaining the absorbed water.

Among other fibrous materials which could advantageously be used may be mentioned by way of example microcrystalline cellulose and high density polyethylene fibres. However, it is preferred that the fibrous material is a hydrophilic one which has strong water retention properties.

The above materials are mentioned by way of example only, and anyone skilled in the art could select other materials on the basis of the desired properties stated above. Clearly, when it is to be ingested, the fibrous powder should be pharmaceutically or veterinarily acceptable.

The capsules of the invention may be manufactured using the techniques normally used in the art. The requisite quantity of fibrous materials is added to the gelatin either before, during or after dissolving it, for example in the form of an aqueous suspension, and the molten gelatin bath stirred to obtain an homogeneous suspension from which the capsule shells are made in the usual way.

The beneficial effects of the invention are clearly demonstrated by the following example.

EXAMPLE

Batches of No. 0 capsules were made with gelatin into which 1% and 2% Croscarmellose had been incorporated by addition as a 1% w/v suspension. A number of standard capsules and fibre-containing capsules were each filled with 150 mgm of Carnitine, a highly hygroscopic crystalline solid. Samples of each batch of capsules were tested at intervals of 5 minutes by visual inspection for cracked or split capsules.

The experimental capsules showed greatly improved resistance to embrittlement. Capsules prepared from gelatin containing 1% Croscarmellose exhibited no splitting, while those made from gelatin with 2% Croscarmellose showed only very low incidence of splitting in these extreme conditions, compared to the standard capsules, all of which became brittle and cracked at between 10 minutes and 2 hours.

I claim:

1. A two-piece hard capsule shell having improved embrittlement properties comprising an admixture of gelatin and a pharmaceutically or veterinary acceptable hydrophilic fibrous material, wherein the fibres in the fibrous material have lengths of up to about 1000 microns.

2. A capsule shell of claim 1 wherein the fibrous material comprises up to about 10% of the admixture.

3. A capsule shell of claim 2 wherein the fibrous material comprises from about 0.5% to about 2.0% of the admixture.

4. A capsule shell of claim 1 wherein the fibrous material is cross-linked carboxymethylcellulose sodium.

5. A capsule shell of claim 2 wherein the fibrous material is cross-linked carboxymethylcellulose sodium.

6. A capsule shell of claim 1 wherein the lengths of the fibres are from about 50 microns to about 300 microns.

7. A capsule shell of claim 2 wherein the lengths of the fibres are from about 50 microns to about 300 microns.

8. A capsule shell of claim 1 wherein the lengths of the fibres are from about 50 microns to about 300 microns.

9. A capsule shell of claim 2 wherein the lengths of the fibres are from about 50 microns to about 300 microns.

10. A capsule shell of claim 5 wherein the lengths of the fibres are from about 50 microns to about 300 microns.

11. A capsule shell of claim 3 wherein the fibrous material is cross-linked carboxymethylcellulose sodium wherein the fibres in the fibrous material are from about 50 microns to about 300 microns in length.

12. A capsule shell of claim 1 which contain a hygroscopic or deliquescent component.

* * * * *